United States Patent
Siew et al.

(10) Patent No.: US 11,723,588 B2
(45) Date of Patent: Aug. 15, 2023

(54) DEVICE FOR APNEA DETECTION, SYSTEM AND METHOD FOR EXPEDITING DETECTION OF APNEA EVENTS OF A USER

(71) Applicant: Advanced Analyzer Technologies Pte Ltd, Singapore (SG)

(72) Inventors: Sai Kit Siew, Singapore (SG); Siew Hua Chua, Singapore (SG)

(73) Assignee: Advanced Analyzer Technologies Pte Ltd, Singapore (SG)

( * ) Notice: Subject to any disclaimer, the term of this patent is extended or adjusted under 35 U.S.C. 154(b) by 420 days.

(21) Appl. No.: 16/904,555

(22) Filed: Jun. 17, 2020

(65) Prior Publication Data

US 2021/0145357 A1 May 20, 2021

(30) Foreign Application Priority Data

Nov. 18, 2019 (SG) .......................... 10201910779Y

(51) Int. Cl.
*A61B 5/00* (2006.01)
*A61B 5/0205* (2006.01)
(Continued)

(52) U.S. Cl.
CPC .......... *A61B 5/4818* (2013.01); *A61B 5/0022* (2013.01); *A61B 5/0205* (2013.01); *A61B 5/113* (2013.01); *A61B 5/1455* (2013.01); *A61B 5/6814* (2013.01); *A61B 5/6826* (2013.01); *A61B 5/7285* (2013.01);
(Continued)

(58) Field of Classification Search
None
See application file for complete search history.

(56) References Cited

U.S. PATENT DOCUMENTS

| 5,995,827 A * | 11/1999 | Gitlin .................... H04M 1/724 |
| | | 455/212 |
| 6,498,652 B1 | 12/2002 | Varshneya et al. |
| (Continued) | | |

FOREIGN PATENT DOCUMENTS

| CN | 1700849 A | 11/2005 |
| CN | 104545888 A | 4/2015 |
| (Continued) | | |

*Primary Examiner* — Matthew Kremer
*Assistant Examiner* — Matthew Eric Ogles

(57) ABSTRACT

Example embodiments include devices and systems that detect apnea events of a user. The device includes a first sensor configured beside the head of the user for capturing snoring sounds of the user, a second sensor configured on one finger of the user for capturing cardiovascular parameters of the user, a third sensor configured under the trunk of the user for capturing e breathing movements of the user, a data recorder that is connected with the first sensor, the second sensor and the third sensor for receiving recordings therefrom, and a clock for synchronizing the recordings in real time. The recordings include one or more breathing events including snoring events, heart rate and $SPO_2$ conjunction spikes, and breathing movement cessations. The time periods that apnea events are impossible can be excluded according to a combination of the breathing events, and the apnea events can be detected thereafter.

11 Claims, 8 Drawing Sheets

(51) Int. Cl.
 *A61B 5/113* (2006.01)
 *A61B 5/1455* (2006.01)

(52) U.S. Cl.
 CPC ..... *A61B 2562/06* (2013.01); *A61B 2562/182* (2013.01); *A61B 2562/223* (2013.01)

(56) References Cited

U.S. PATENT DOCUMENTS

| | | | | |
|---|---|---|---|---|
| 2003/0095263 | A1* | 5/2003 | Varshneya | A61B 5/4818 356/477 |
| 2004/0022393 | A1* | 2/2004 | Jones | H04R 3/00 381/56 |
| 2004/0054269 | A1* | 3/2004 | Rantala | A61B 5/14551 600/322 |
| 2004/0189475 | A1* | 9/2004 | Cooper | A61B 5/6892 340/573.1 |
| 2008/0221399 | A1* | 9/2008 | Zhou | G16Z 99/00 600/301 |
| 2012/0016219 | A1* | 1/2012 | Fujii | A61B 5/6826 600/324 |
| 2013/0109931 | A1 | 5/2013 | Ng et al. | |
| 2014/0350355 | A1* | 11/2014 | Aisic | A61B 7/003 600/301 |
| 2016/0120465 | A1 | 5/2016 | Parfenova et al. | |
| 2017/0303825 | A1* | 10/2017 | Martinson | A61B 5/112 |
| 2018/0333558 | A1* | 11/2018 | Levendowski | A61B 5/389 |
| 2019/0192047 | A1* | 6/2019 | Stamatopoulos | G10L 25/66 |

FOREIGN PATENT DOCUMENTS

| | | | |
|---|---|---|---|
| CN | 107095645 A | 8/2017 | |
| CN | 109745002 A | 5/2019 | |
| CN | 112450880 B | 11/2022 | |
| EP | 2859839 A1 * | 4/2015 | ........ A61B 5/0006 |
| TW | 201622990 A | 7/2016 | |
| TW | I754458 B | 2/2022 | |
| WO | 2008011058 A2 | 1/2008 | |

* cited by examiner

DEVICE FOR APNEA DETECTION, SYSTEM AND METHOD FOR EXPEDITING DETECTION OF APNEA EVENTS OF A USER

CROSS REFERENCE TO RELATED APPLICATIONS

The present application claims the benefit of Singapore Patent Application No. 10201910779Y filed on Nov. 18, 2019, the contents of which are incorporated herein by reference in their entirety.

FIELD OF THE INVENTION

The present invention relates to an electronic device, and more particularly to a device that detects and counts apnea events.

BACKGROUND

Sleep apnea is a serious sleep disorder that occurs when a user's breathing is interrupted during sleep. People with untreated sleep apnea stop breathing repeatedly during their sleep, sometimes hundreds of times, which causes insufficient oxygen supplied to the brain and the rest of the body. If left untreated, sleep apnea can increase the risk of health problems, such as hypertension, diabetes and high chlorestrol, etc. In addition, untreated sleep apnea may result in poor performance in everyday activities, such as at work and school, motor vehicle crashes, and academic underachievement in children and adolescents.

New devices that provides a low cost and convenient way to assist in detection of the sleep apnea will meet the potential patients' needs, and solving technological problems.

SUMMARY OF THE INVENTION

Example embodiments include devices and systems that detect apnea events of a user. The device includes a first sensor configured beside the head of the user for capturing snoring sounds of the user, a second sensor configured on one finger of the user for capturing cardiovascular parameters of the user, a third sensor configured under the trunk of the user for capturing e breathing movements of the user, a data recorder that is connected with the first sensor, the second sensor and the third sensor for receiving recordings therefrom, and a clock for synchronizing the recordings in real time. The recordings include one or more breathing events including snoring events, heart rate and SPO2 conjunction spikes, and breathing movement cessations. The time periods that apnea events are impossible can be excluded according to a combination of the breathing events, and the apnea events can be detected thereafter.

Example embodiment includes a system for detecting apnea events of a user. The system includes a first sensor configured to capture snoring sound of the user, a second sensor configured to capture cardiovascular parameters of the user, a third sensor configured to capture breath motion cessations of the user, a data recorder connected with the first sensor, the second sensor and the third sensor for receiving the sensors' recordings, and a computer system. The data recorder includes a real time clock to synchronize the sensors' measurements and communicates with the computer. The computer system includes a processor and a non-transient computer-readable storage medium which stores thereon instructions that when executed cause the processor to receive measurements from the data recorder, extract one or more breathing events including snoring events, heart rate and SPO$_2$ conjunction spikes, breathing movement cessations from the measurements, exclude time periods that an apnea is impossible according to a combination of the breathing events, and detect the apnea events outside the excluded time periods.

Example embodiment further includes a system for capturing breath movement cessations of a user when the user is sleeping. The system includes a sensing unit, a data recorder, and a signal processing unit. The sensing unit measures one or more of a snoring sound of the user, cardiovascular parameters of the user, and breath movement cessations of the user. The data recorder includes a real time clock and connects with the sensing unit for recording measurements from the sensing unit and synchronizing the measurements in time by the clock. The signal processing unit extracts breathing events from the synchronized measurements and excludes time periods that an apnea is impossible according to the breathing events so that the detection of the apnea events is expedited.

Example embodiment further includes a method executed by a computer for detecting apnea events of a user. The method includes the following steps: receiving measurements captured from a plurality of sensors when the user is sleeping, the measurements including snoring sounds, cardiovascular parameters and breathing movements of the user; synchronizing the recordings in the data recorder by a clock; extracting a plurality of breathing events including snoring events, heart rate and SPO2 conjunction spikes, and breathing movement cessations from the recordings; excluding time periods that an apnea is impossible according to a combination of the breathing events; and detecting the apnea events outside the excluded time periods.

Other example embodiments are discussed herein.

DETAILED DESCRIPTION

Figure 1:
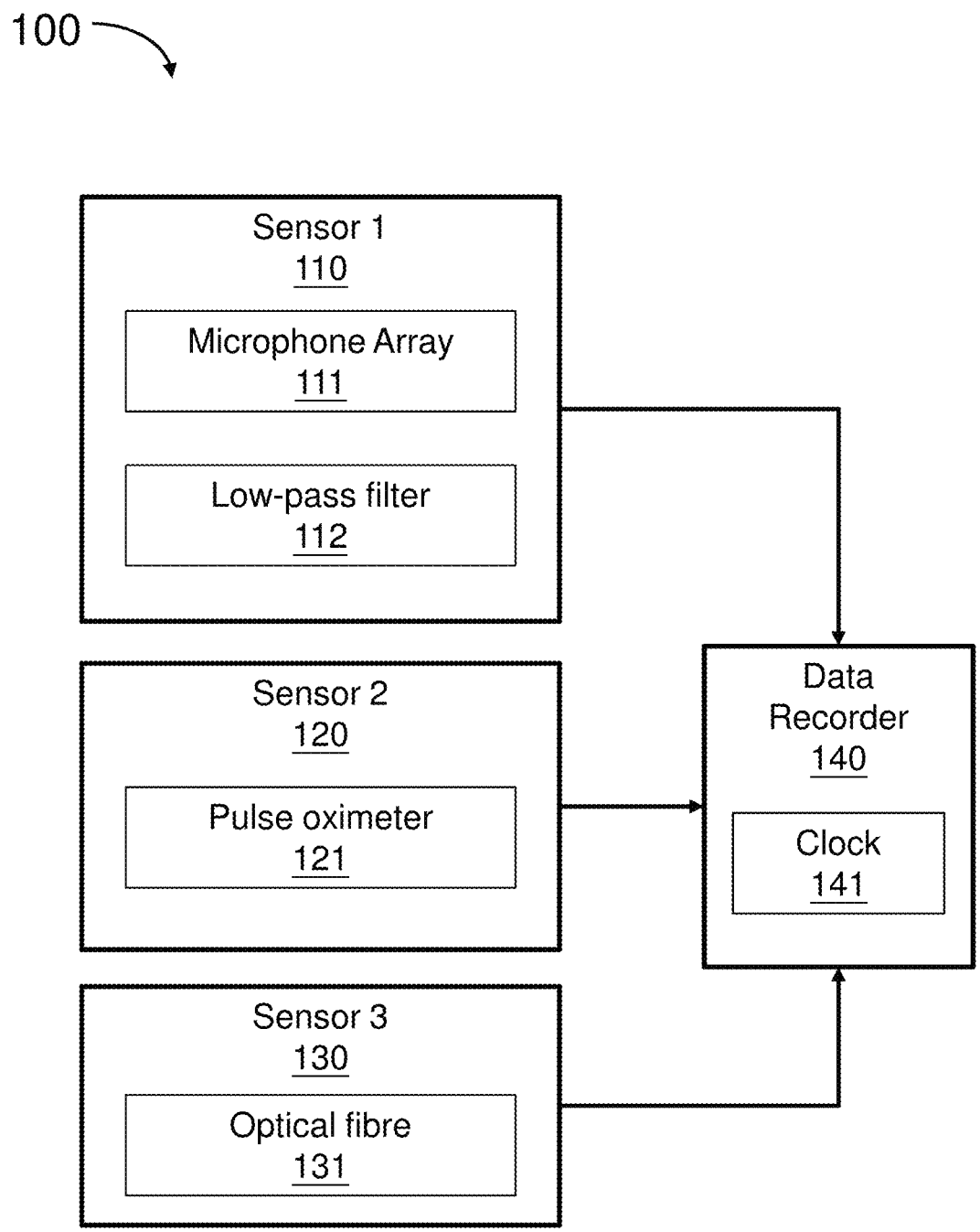
FIG. 1 illustrates a device for detecting sleep apnea in accordance with an example embodiment.

Example embodiments relate to a device with novel structure and improved performances for monitoring breathing of a person during sleeping.

The current Gold standard for the detection of sleep-disordered breathing is the Polysomnography (PSG) test. The PSG test requires the patient under test to sleep over-night in a sleep laboratory under the observation of a registered sleep technologist (RST) with sensor data recorded for post-event processing.

During the PSG test, the patient is hooked up to the equipment via adhesive tape and elastic tension belts. Typically, two pressure sensors are attached across the patient's abdomen and thorax for detecting the breathing movements of the patient. Air-flow sensors are inserted into the patient's nostrils to measure the rate of air-flow into the patient's lungs. Electrical signal sensors are attached to the head and chest of the patient to measure the brain waves as well as the heart movements of the patient. Microphones are attached to the patient's neck below the jaw and above the patient's head to monitor the snoring. The recorded data over the night are then processed the next day by a RST to decipher the information.

The cost of setting up a PSG Test Sleep Laboratory is high due to the complicated and expensive equipment. Consequently, there are not enough such set-ups in third world or lesser developed countries, and the queuing time for a test can stretch from several weeks to months on end.

The Apnea-Hypopnea Index (AHI) is an index used to indicate the severity of sleep apnea. It is represented by the number of apnea events per hour of sleep. The apneas, i.e. pauses in breathing, must last for at least 10 seconds and be associated with a decrease in blood oxygenation. Apnea is classified as mild for 5 to 15 AHIs/hour, moderate for 16 to 30 AHI/hour; and severe for >30 AHIs/hour. The counting is currently manually done by RSTs reviewing the historical time charts of the patient's sleep over the course of the night, which is a tedious and time-consuming work as approximately 16 sensors are charted for examination.

One or more example embodiments solve one or more of the technical problems associated with conventional sleep test devices and methods as set forth above. One or more example embodiments achieve low-cost and portable breathing monitoring devices that can be used as a pre-test filter for the high priced PSG test. Patients who may have sleep apnea, instead of paying the high price of the PSG Test, are pre-tested at home first using the portable device, and ensure that only the afflicted are tested further.

Example embodiments recognize that even patients with severe sleep apnea breathe normally most of the time. Instead of measuring the time periods that apnea occurs, example embodiments monitor the time periods that the person is breathing. This masks away most periods where apnea events are impossible so that the reviewing work need to done by RSTs are greatly decreased, and thus the efficiency of AHI diagnosis is increased accordingly.

Example embodiments incorporate four sensor measurements, including the snoring sounds, heart rate per minute, oxygen saturation ($SPO_2$) and the breath movement cessations of the patient over the course of the sleeping, working in conjunction to assist in computing the AHI of the patient. The resulting chart is interpreted to give a simple AHI count during the sleeping, which makes a useful aid for the doctors to detect sleep-disordered breathing with AHI as a discrete measure. Furthermore, example embodiments are non-inhibitive and portable as no wires need to be tied to the patient under test, only the oximeter is worn on the patient's finger.

In one example embodiments, the device to detect sleep apnea of a user when the user is sleeping includes a first sensor that captures snoring sound of the user, a second sensor that captures cardiovascular parameters including heart rate and $SpO_2$ value of the user, a third sensor that captures breath movement cessations of the user, and a data recorder that is connected with the first sensor, the second sensor and the third sensor for receiving recordings therefrom. The data recorder includes a real time clock to synchronize the measurements in time. The first sensor's recording includes snoring events. The second sensor's recordings include heart rate and $SPO_2$ conjunction spikes. The third sensor's recording includes breath movement cessations. Time periods that the user is breathing normally can be determined according to a combination of the snoring events, the heart rate and $SPO_2$ conjunction spikes, and the breath movement cessations.

In one example embodiment, a system to detect sleep apnea of a user when the user is sleeping includes the device described above and a computer system. The computer system receives the sensors' recordings from the data recorder and analyze the recordings to extract the snoring events, the heart rate and $SPO_2$ conjunction spikes, and the breathing movement cessations so that the time periods that the user is breathing normally are determined.

FIG. 1 illustrates a device 100 to detect sleep apnea in accordance with an example embodiment.

The device 100 includes a first sensor 110, a second sensor 120, a third sensor 130 and a data recorder 140. The first sensor 110, the second sensor 120, and the third sensor 130 are connected with the data recorder 140 so that the data recorder 140 receives recordings for the sensors 110, 120 and 130. The data recorder further includes a real time clock, by which the recordings received from the sensors 110, 120 and 130 are synchronized, so that phases in time that apnea is impossible can be masked out.

The first sensor 110 includes a microphone array 111 and a low-pass filter 112 that is connected with the microphone array 111. The low-pass filter 112 filters the signals captured by the microphone array 111 before the signals are sent to the data recorder 140. The microphone array 111 includes one or more microphones.

The second sensor 120 includes a pulse oximeter 121 that is capable of measuring heart rate and oxygen saturation continuously. The third sensor 130 includes an optical fiber 131. The optic fiber 131 is flexible and is configured to generate light loss when there are body movements of a human subject lying on top of the sensor 130, so that the sensor 130 outputs a measurement according to the body movement.

In an example embodiment, instead of using the pulse oximeter 121, the device 100 includes two separate sensors, one for measuring the heart rate and the other for measuring the oxygen saturation. In other example embodiments, other sensors for measuring the required cardiovascular parameters of the user can be applied.

In an example embodiment, each sensor 110, 120, and 130 includes a wireless transmitter, and the data recorder 140 includes a wireless receiver, so that the data recorder 140 receives the recordings from the sensors 110, 120, and 130 by wireless transmission. In another example embodiment, one or more sensors 110, 120, and 130 are connected with and powered by the data recorder 140 by wires.

In one example embodiment, each sensor measurements is tagged with a time generated from the real time clock. Since each data recording has a time tag, the data of all the sensor recordings can be synchronized by a processor according to the time tag.

The sensors described above and in FIG. 1 are for example only. In other example embodiment, the sensors for recording the snoring sounds, the cardiovascular parameters, and the breathing motions may be other sensors than those described in FIG. 1.

Figure 2:
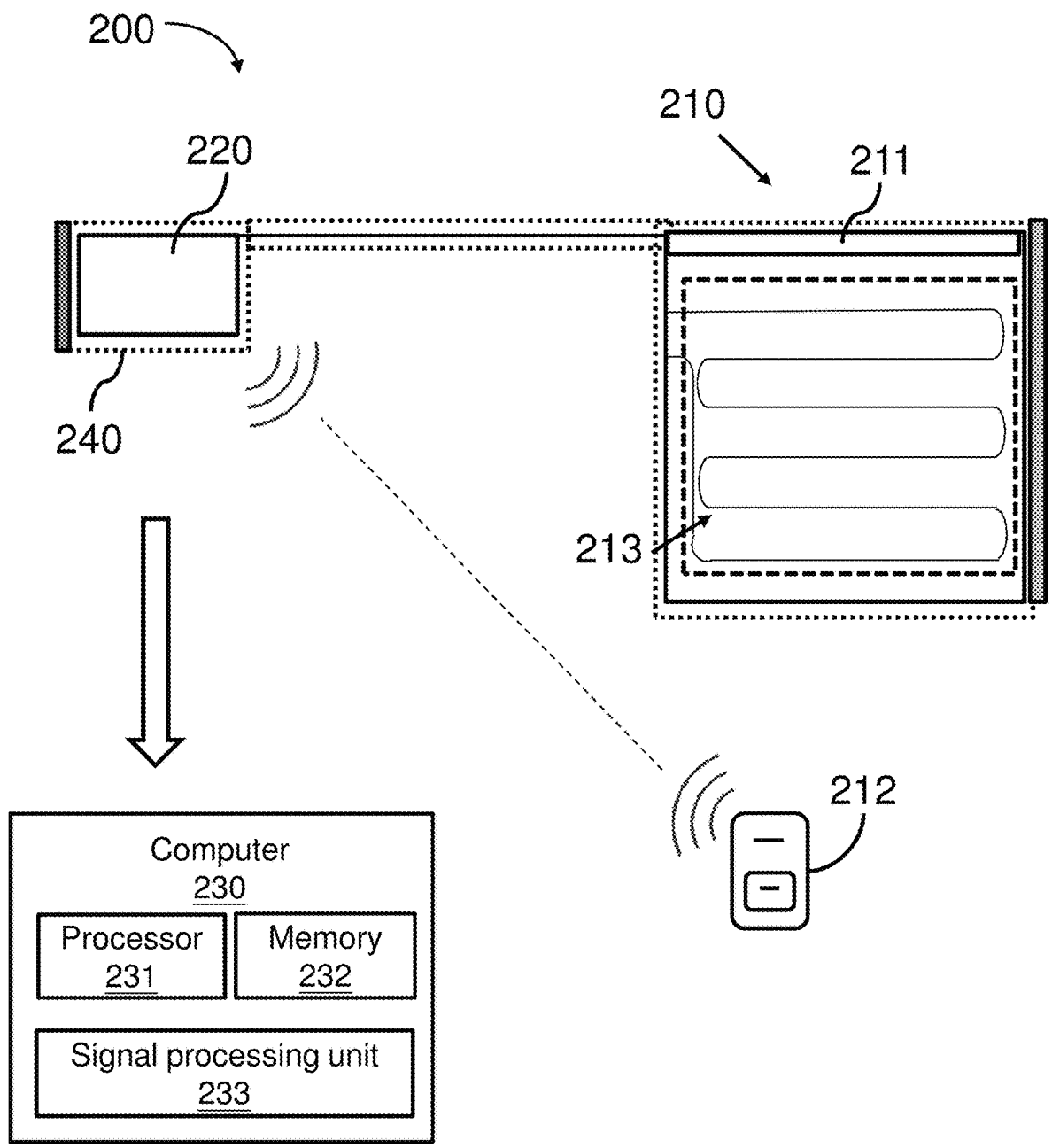
FIG. 2 illustrates a system for detecting sleep apnea in accordance with an example embodiment.

FIG. 2 is a system 200 for monitoring breathing in accordance with an example embodiment.

The system 200 includes a sensing unit 210, a data recorder 220 and a computer system 230. The data recorder 220 is connected with the sensing unit 210 for receiving measurements therefrom. The data recorder 220 includes a real time clock for making measurements synchronization. The computer 230 includes a processor 231, a memory 232 and a signal processing unit 233. The computer 230 receives data from the data recorder 220 and carries out computation and analysis on the received data.

The sensing unit 210 is used for measuring a plurality of physiological properties of a user when the user is sleeping, which includes a first sensor 211 for measuring snoring sound of a user when the user, a second sensor 212 for measuring cardiovascular parameters of the user, a third sensor 213 for measuring breathing movements of the user.

By way of example, the first sensor 211 includes a microphone array and a low-pass filter, the second sensor 212 includes an oximeter, and the third sensor 213 includes an optical fiber motion sensor.

The sensors 211 and 213 are connected with the data recorder 220 by wires for data transmission and power supply. For example, the wires are twisted pair wire cables that reduces electromagnetic radiation (EMR) from the pair and improve rejection of external electromagnetic interference. The sensor 212 is self-powered and connected with the data recorder 220 wirelessly for data transmission.

The data recorder 220 is a single board computer (SBC) with a real-time clock. It further includes a wireless receiver for receiving data from the sensor 212, a memory card for storing the received data, and a battery supply to power the system 200 for around 10 hours. Data from the sensors are recorded onto the memory card to be processed in the computer 230. By way of example, the memory card is a flash memory card and the wireless receiver is a blue tooth low energy transducer.

In some example embodiment, the data recorder 220 further includes signal conditioners for pre-processing the data received from the sensors 211, 212 and 213, such as amplification, filtering, converting, range matching, isolation or any other processes required to make sensor output suitable for processing. The data recorder 220 also includes an encryption method for protecting the received data, for example, by using Advanced Encryption Standard (AES) algorithm.

The sensors 211, 213 and the data recorder 220 are covered in a RF absorbent sleeve, only the antenna of the receiver is exposed, so as to reduce the EMR to the person in test.

The computer system 230 stores the data received from the data recorder 220 and performs a method to extract breathing events from the data in the signal processing unit 233 by the processor 231. The breathing events includes one or more of the snoring events that snoring sound is recorded, the heart rate and $SPO_2$ conjunction spikes that the heart rate and $SPO_2$ value spiked upward in conjunction after decrease, and breath movement cessations that the chest of the user in test stops moving up and down. The computer system 230 further determine time periods that the user is considered to be breathing according to a combination of the snoring events, heart rate and $SPO_2$ conjunction spikes and the breath movement cessations of the user.

First, the time periods during the snoring events is taken to disprove possibility of an apnea event, because when the user is snoring, air enters the body and vibrates across the soft palate. The time periods less than 10 seconds between two successive snoring events are also excluded from an apnea event according to the definition of apnea. By this step, a large portion of the test duration is masked away if the user snores during sleep.

Further, in an apnea event, both measurements of the heart rate and the $SPO_2$ gradually decrease until the patient's brain instructs a strong arousal to the heart resulting in a strong upswing in the heart-rate and $SpO_2$ measurements. Therefore, a conjunction spike often marks the end of an apnea event. If the conjunction spike is within 10 seconds of a snoring event or other conjunction spikes, the time periods between these events are masked out from the apnea detection, as there cannot be apnea events within according to the definition of apnea.

Further yet, when the patient under test ceases breathing, there is no breathing movement and the optical fiber motion sensor 213 records the cessation of breathing movement. The breath motion cessation usually marks the start of the apnea event. In one example embodiment, the less than 10 seconds breath motion cessation phases are excluded from an apnea event.

In one example embodiment, after masking out the time periods where apnea cannot exist based on a combination of the snoring events and the conjunction spikes, the left conjunction spikes outside the no apnea events zone are examined individually combining with the breath motion cessation recordings. If the breath motion cessation event lasts less than 10 seconds before the subsequent conjunctive spike appears, the events are discarded as normal breathing, while those greater than 10 seconds are counted for the apnea event count.

In one example embodiment, time periods that the apnea is impossible can be determined by analyzing a combination of the snoring events, the heart rate and $SPO_2$ conjunction spikes, and the breathing movement cessations. In other example embodiment, one or two of the breathing events, such as the snoring events, the heart rate and $SPO_2$ conjunction spikes, are analyzed to exclude the time periods that an apnea is impossible. When the time periods that the user is breathing normally have been determined, they can be masked away from the sensors' measurement chart. As a result, the RSTs can focus on a small portion of the chart where apnea events are expected. Their workload is greatly reduced so that the efficiency of diagnosis increases.

Figure 3A:
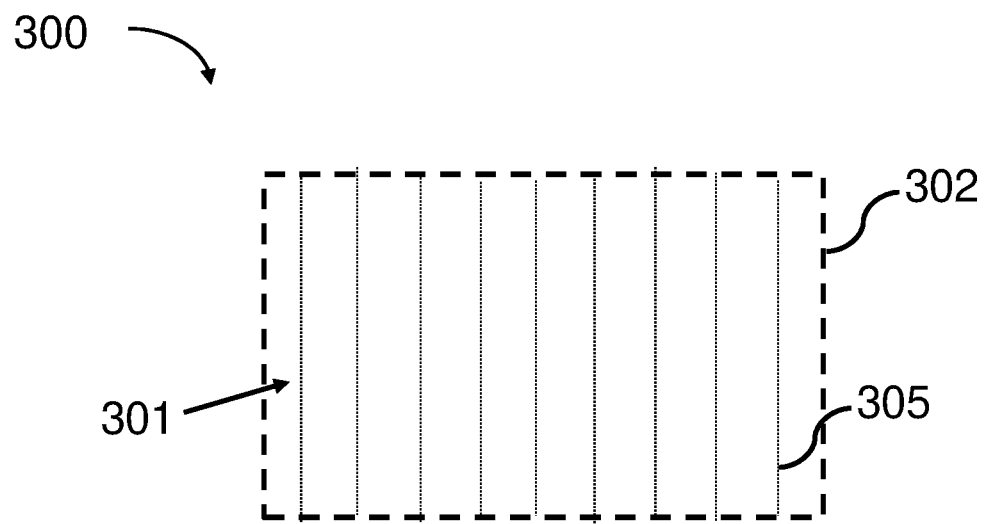
FIG. 3A illustrates an optical fiber motion sensor in accordance with an example embodiment.
Figure 3B:
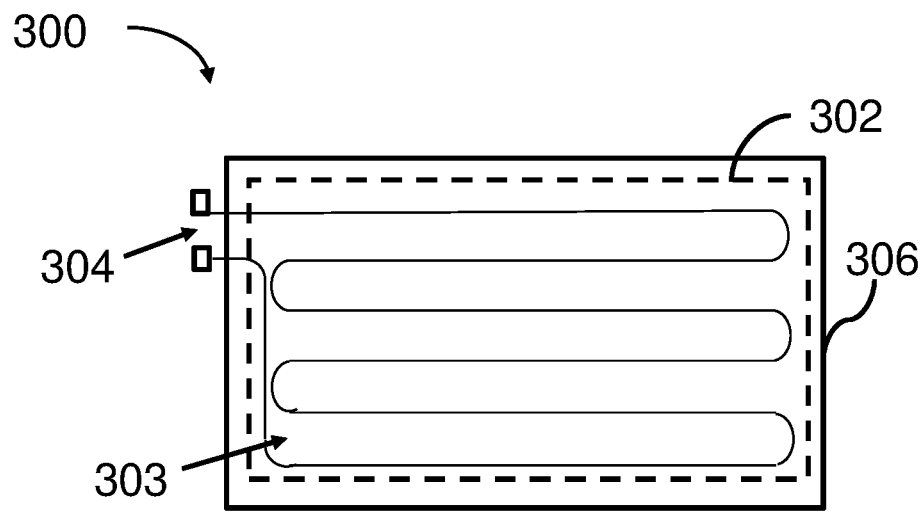
FIG. 3B illustrates an optical fiber motion sensor in accordance with an example embodiment.

FIGS. 3A and 3B illustrates an optical fiber motion sensor 300 in accordance with an example embodiment.

The optical fiber motion sensor 300 includes an upper frame 302 that is stiff for a user to sleep on, a lower frame 301 that is stiff and includes protrusions, and an optic fiber 303 that is sandwiched between the upper frame 302 and the lower frame 301. The optic fiber has two terminal posts 304 for the light source to be input and sensed, for example, by two twisted pair wires. The optical fiber motion sensor 300 further includes an outer waterproof jacket 306 that covers the upper frame 302, lower frame 301 and the optical fiber 303.

The lower frame 301 includes a plurality of strips 305, each strip 305 includes a plurality of protrusions (not shown) that distributes evenly thereon. The optic fiber 303 is wound on the strips 301 and fixed by the protrusions. The upper frame 302 are stiff and have elasticity so that it can prevent the optical fiber from fracturing and focus the user's weight upon the optical fibers when the user is lying thereon. As a result, the optic fiber generates light loss corresponding to the breathing movements of the user when the user is lying on the upper frame 302.

Figure 4:
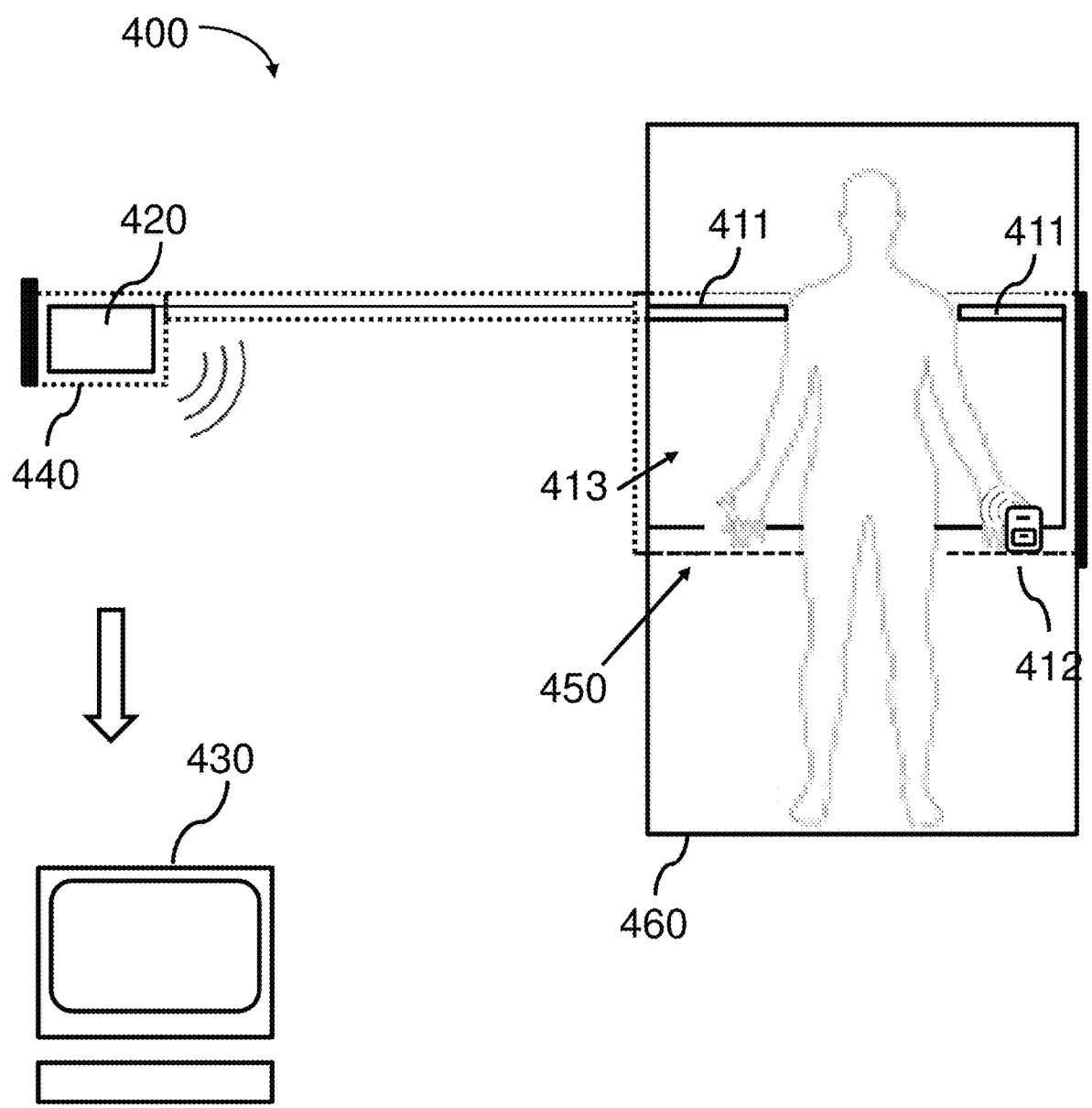
FIG. 4 illustrates a test setup for detecting sleep apnea in accordance with an example embodiment.

FIG. 4 illustrates test setup of a system 400 for detecting sleep apnea in accordance with an example embodiment.

When a user is under test and sleeping on the mat 460, the microphone array 411 is arranged on the mat 460 at the range from the user's head to shoulders so that the snoring sound of the user can be properly captured. By way of example, at least one microphone 411 is arranged at each side of the user's body. The optical fiber motion sensor 413 is arranged on the mat 460 under the user's trunk, i.e., from shoulder to hip, where the breathing movement of the user can be sensed most easily. The oximeter 412 is worn on one finger of the user 450 and it measures the heart rate and the $SPO_2$ value of the user during sleeping.

The microphone array 411 and the oximeter 413 are connected with the data recorder 420 by wires for data transmission and power supply. The oximeter 412 is self-powered and is connected with the data recorder 420 by wireless transmission. When the sleep test is completed, the data recorder 420 outputs the recorded data to a separate computer 430 for data processing and analysis, for example, the computer is a medical computer used by RSTs.

In one example embodiment, the microphone array 411 and the optical fiber motion sensor 413 are integrated in one sheet 450. The data recorder 420 have interfaces for the wires, which enables connection or separation from the sensors. The sheet 450 and the data recorder 420 are covered by a single use cloth, which is replaceable for each user for hygiene.

In one example embodiment, the sheet 450 is foldable, so that the device for detecting breath motion in the system 400 is small-sized and portable. Moreover, the setup of the testing is easy and convenient. Therefore, users to take test are not restricted in the testing lab under supervision of a specialist. They may bring the device to home and take the test by themselves. In addition, during the test, no bundles or wires are wrapped around the user's body, which makes the test natural and comfortable.

Figure 5:
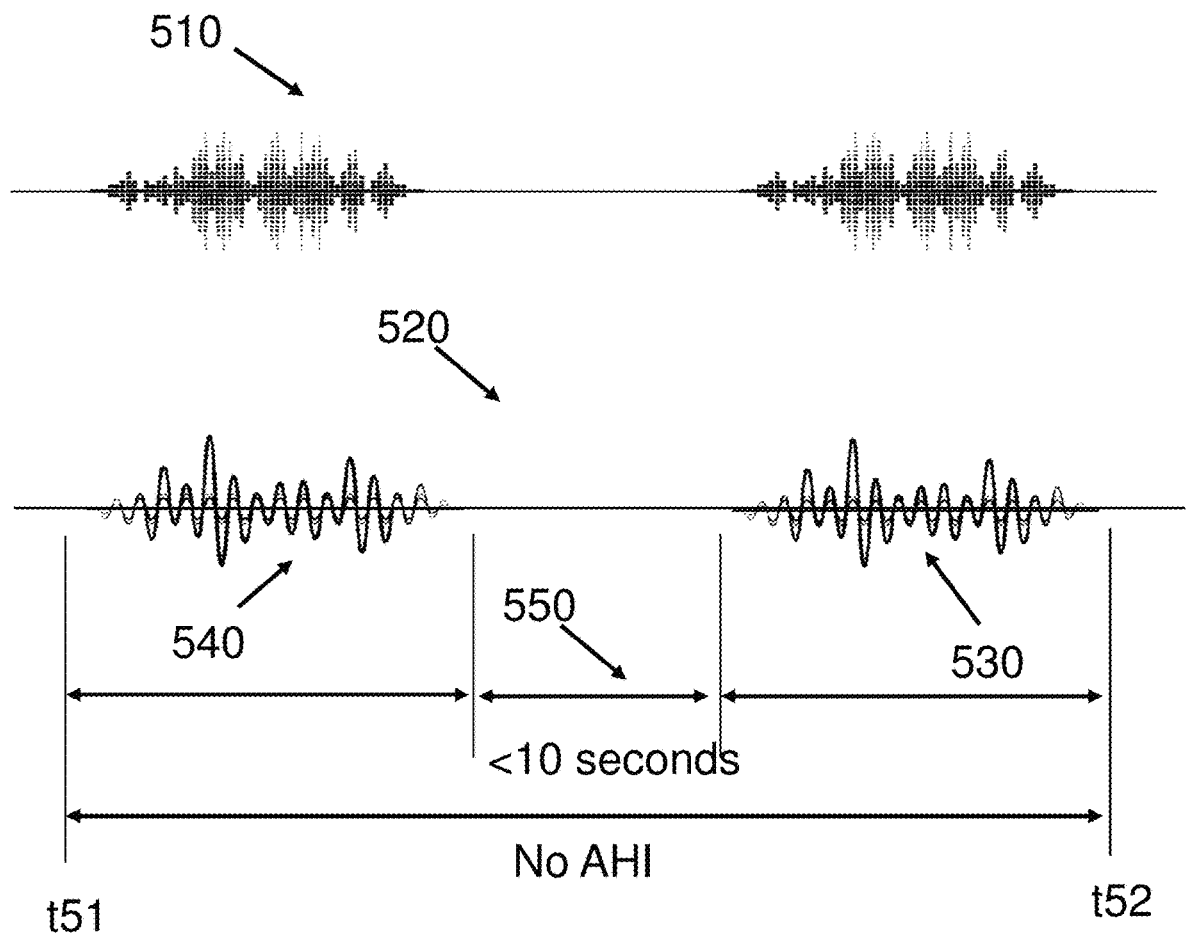
FIG. 5 illustrates extraction of breathing events from snoring sounds in accordance with an example embodiment.

FIG. 5 illustrates extraction of breathing events from snoring sounds in accordance with an example embodiment.

As shown in FIG. 5, the signal 510 is the snoring audio signal captured by the microphone array. The signal 520 is the electronic signal that is filtered from the snoring audio signal 510 by a low-pass filter. The signal 520 includes two snoring events 530 and 540 from time t51 to t52. If the time period 550 between the two snoring events 530 and 540 is less than 10 seconds, it is considered there is no apnea event during t51 to t52, as the user is breathing during the snoring events 530 and 540. Otherwise, it is considered there is one apnea event during t51 to t52.

Figure 6:
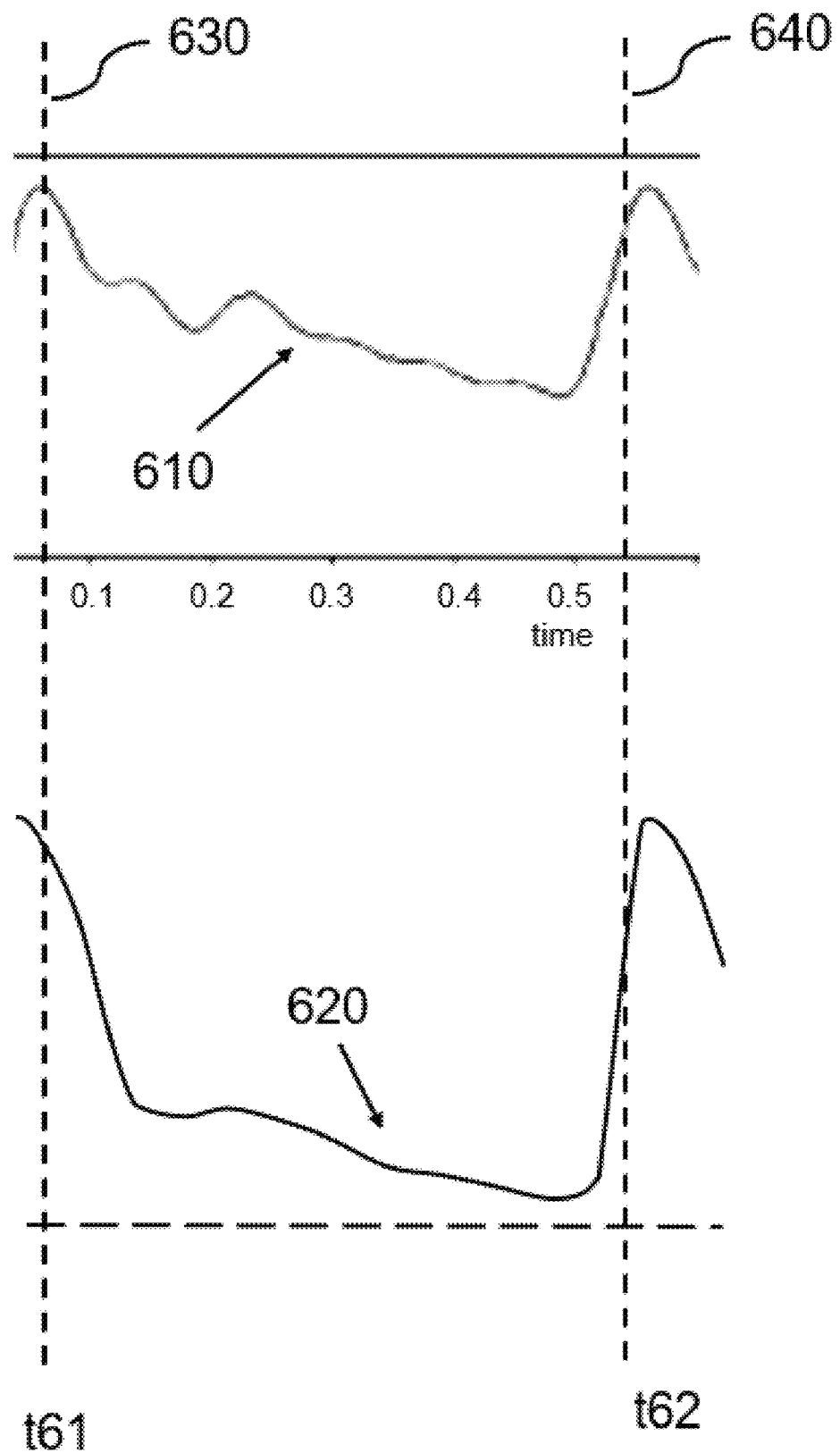
FIG. 6 illustrates extraction of end of apnea from heart rate and oxygen saturation (SPO$_2$) value in accordance with an example embodiment.

FIG. 6 illustrates extraction of breathing events from heart rate and oxygen saturation ($SPO_2$) conjunction spikes in accordance with an example embodiment.

As shown in FIG. 6, the curve 610 shows the heart rate per minute and the curve 620 shows $SPO_2$ value of the user under test. Both curves 610 and 620 spike upwards at time t62 after decreasing from time t61. That indicates the end of an apnea event when the user restores breathing. The start of the apnea event is expected to be within a pre-determined time period before the end of the apnea event. For example, the pre-determined time period is between 10 seconds and 60 seconds. Except for the estimated time period of the apnea, in other time periods the user is considered as breathing normally.

In another situation, if two successive conjunction spikes are extracted and the time period there between is less than 10 seconds, the time period is excluded from an apnea event.

Figure 7:
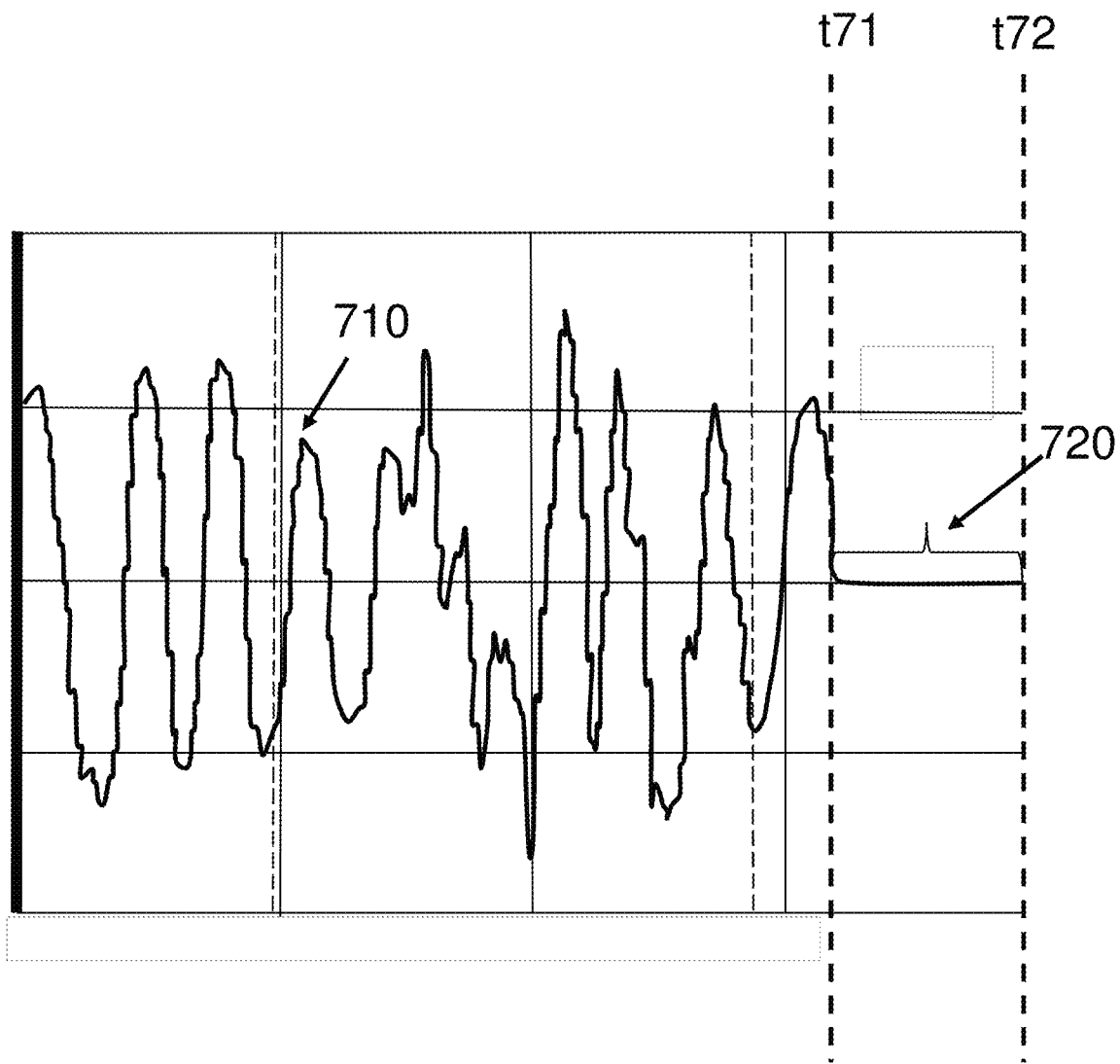
FIG. 7 illustrates extraction of start of apnea from breathing movement cessations in accordance with an example embodiment.

FIG. 7 illustrates extraction of breathing events from breathing movements in accordance with an example embodiment.

When the user is breathing normally, a breathing movement of the user should be detected by the motion sensor, as depicted in the curve 710. Accordingly, a cessation of the breathing movement is considered to signal the start of an apnea event. As shown in FIG. 7, the time t71 is considered as the start of an apnea event.

In one example embodiment, if the movement cessation period 720 is less than 10 seconds, an apnea event is excluded from the time period. In another example embodiment, a pre-determined period from the cessation start time t71 is estimated to be the time period of an apnea. For example, the pre-determined time period is within 10 seconds to 60 seconds.

In one example embodiment, a combination the breathing movement cessation, together with the decrease of heart rate and $SPO_2$ value, is used to confirm the start of the apnea event.

Figure 8:
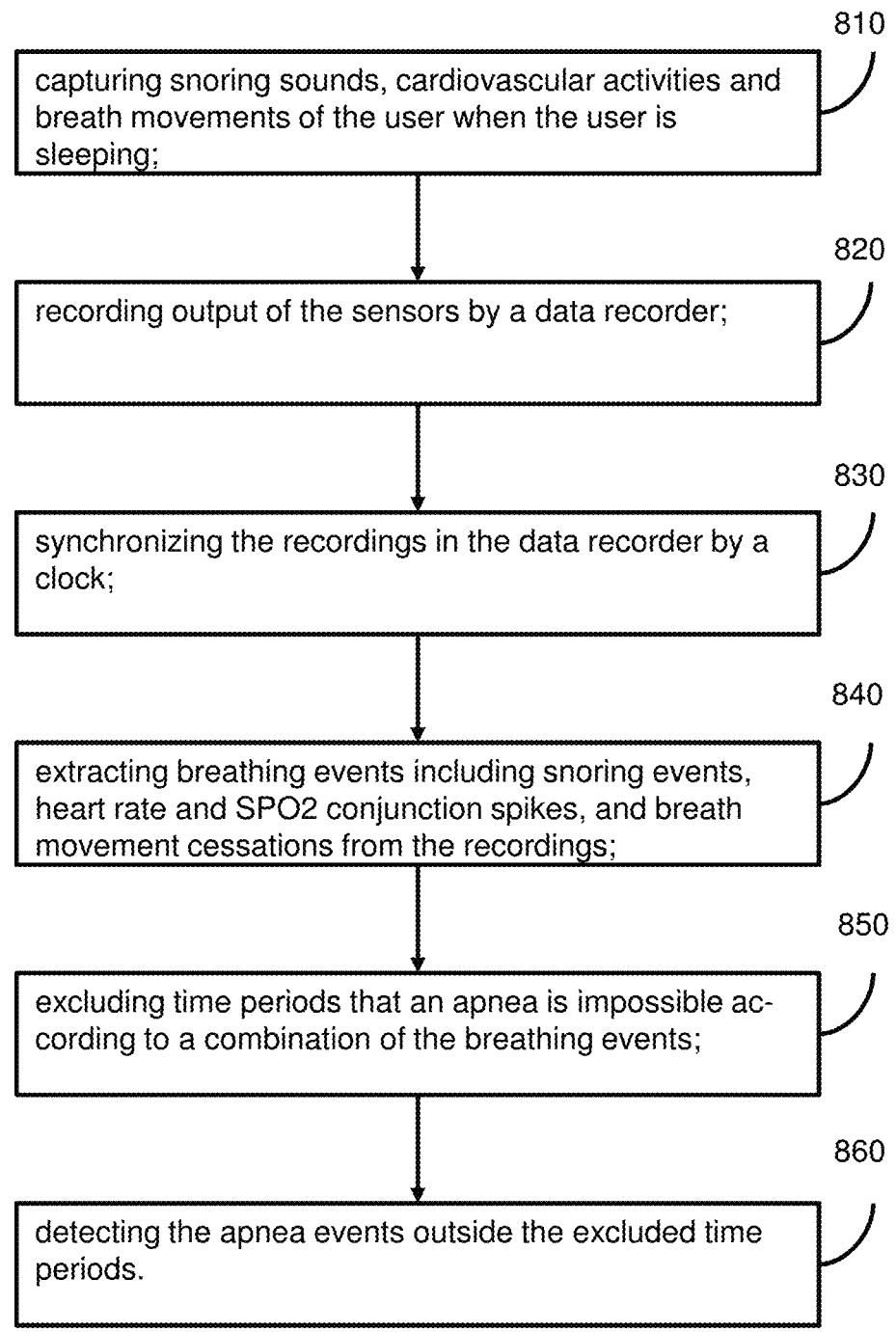
FIG. 8 illustrates a method for detecting apnea events for a user in accordance with an example embodiment.

FIG. 8 illustrates a method for detecting apnea events for a user.

Block 810 states capturing snoring sounds, cardiovascular parameters and breathing movements of the user when the user is sleeping.

In one example embodiment, the snoring sounds are captured by an audio sensor; the cardiovascular parameters are captured by an oximeter; and the breathing movements of the user is captured by a motion sensor.

Block 820 states recording output of the sensors by a data recorder.

In one example embodiment, the data recorder receives signals captured by sensors by wireless transmission.

Block 830 states synchronizing the recordings in the data recorder by a clock.

In one example embodiment, the clock is a precision time protocol that can deliver highly accurate time to synchronize the recordings, which includes signals received by the data recorder from different sensors.

Block 840 states extracting breathing events including snoring events, heart rate and SPO2 conjunction spikes, and breathing movement cessations from the recordings.

In one example embodiment, the breathing events are extracted by a computing device that includes a processing unit.

Block 850 states excluding time periods that an apnea is impossible according to a combination of the breathing events.

In one example embodiment, the following time periods are considered as no apnea periods, including: (1) the time period of each snoring event, (2) time period between two snoring event that is less than a pre-determined length of time; (3) time period between a conjunction spike and a snoring event that is less than a pre-determined length of time, (4) time period between two conjunction spikes that is less than the pre-determined length of time, and (5) time period of the breathing movement cessation that is less than the pre-determined length of time. In this step, most of the time periods are excluded as no apnea, since even the patient with severe sleep disorder breathes normally most of the time.

In one example embodiment, the pre-determined length of time is 10 seconds.

Block 860 states detecting the apnea events outside the excluded time periods.

In one example embodiment, after excluding the no apnea time period, the left time periods that likely contain an apnea is further examined. For example, if the time period of the breathing movement cessation is greater than the pre-determined length of time before a conjunctive spike appears, it is considered as an apnea event.

In one example embodiment, the number of the apnea events are counted per hour. In other example embodiment, the average counts of the apnea events per hour are calculated by dividing the total number by the sleeping hours.

As used herein, "a real time clock" refers to a clock that has its own power battery, runs independent of other circuitry and provides a time tag in real time.

As used herein and in the claims, "a snoring event" refers to a breathing stage during which a continuous snoring sound is recorded.

As used herein and in the claims, "a heart rate and $SPO_2$ conjunction spike" refers to a signal where the spike of a heart rate and the spike of the $SPO_2$ appear simultaneously.

As used herein and in the claims, "breathing movements" refers to movements of a human body that are caused by breathing.

The method of the present disclosure may be implemented in the form of a software application running on a computer system. Further, portions of the methods may be executed on one such computer system, while the other portions are executed on one or more other such computer systems. Examples of the computer system include a mainframe, personal computer, handheld computer, server, etc. The software application may be stored on a recording media locally accessible by the computer system and accessible via a hard wired or wireless connection to a network, for example, a local area network, or the Internet.

The method and apparatus in accordance with example embodiments are provided as examples, and examples from one method or apparatus should not be construed to limit examples from another method or apparatus. Further, methods and apparatus discussed within one figure can be added or exchanged with methods and apparatus in other figures. Further yet, specific numerical data values (such as specific quantities, numbers, categories, etc.) or other specific information should be interpreted as illustrative for discussing example embodiments. Such specific information is not provided to limit example embodiment.

What is claimed is:

1. A device for detecting sleep apnea events of a user, comprising:
   a first sensor for capturing snoring sound of the user;
   a second sensor for capturing cardiovascular parameters of the user;
   a third sensor for capturing breathing movements of the user;
   a data recorder that is connected with the first sensor, the second sensor and the third sensor for recording measurements therefrom; and
   a clock for synchronizing the measurements,
   wherein a dual spike comprises a heart rate spike that occurs simultaneously with a SPO2 spike;
   wherein the measurements include one or more breathing events that comprise snoring events, one or more of the dual spikes, and breathing movement cessations; and
   a signal processing unit that excludes time periods that apnea events are impossible according to a combination of the breathing events, so that detection of the apnea events is expedited,
   wherein the excluded time periods that the apnea events are impossible include:
   a time period of each of the snoring events;
   a time period between two of the snoring events that is less than a pre-determined length of time;
   a time period between one of the dual spikes and one of the snoring events that is less than the pre-determined length of time;
   a time period between two of the dual spikes that is less than the pre-determined length of time; and
   a time period of the breathing movement cessations that is less than the pre-determined length of time;
   wherein the third sensor further comprises:
   an optic fiber;
   an upper frame that is stiff; and
   a lower frame that is stiff and includes protrusions for holding the optic fiber therebetween,
   wherein the optic fiber is sandwiched between the upper frame and the lower frame, so that the optic fiber generates light loss corresponding to the breathing movements of the user when the user is lying on the upper frame.

2. The device of claim 1, wherein the first sensor includes at least one microphone and a low-pass filter that connects with the at least one microphone, and the second sensor includes a pulse oximeter.

3. The device of claim 1, wherein one or more of the first, second, and third sensors communicate with the data recorder by wireless transmission.

4. The device of claim 3, further comprising:
   a sleeve that covers one or more of the first, second, and third sensors and the data recorder, wherein the sleeve is made of a radiofrequency (RF) absorbent material.

5. A system for expediting detection of apnea events of a user, comprising:
   a first sensor configured to capture snoring sound of the user;
   a second sensor configured to capture cardiovascular parameters of the user;
   a third sensor configured to capture breathing movements of the user;
   wherein the third sensor further comprises:
   an optic fiber;
   an upper frame that is stiff; and
   a lower frame that is stiff and includes protrusions for holding the optic fiber,
   wherein the optic fiber meanders between the upper frame and the lower frame, so that the optic fiber generates light loss corresponding to the breathing movements of the user lying on the upper frame;
   a data recorder configured to record measurements of the first sensor, the second sensor and the third sensor, and synchronize the measurements; and
   a computer system that includes a processor and a non-transient computer-readable storage medium,
   wherein the storage medium stores thereon instructions that when executed cause the processor to:
   receive the measurements from the data recorder;
   extract one or more breathing events including snoring events, conjunction spikes, wherein each conjunction spike is a heart rate spike that occurs simultaneously with a SPO2 spike, and breathing movement cessations from the measurements;
   exclude time periods that an apnea event is impossible according to a combination of the breathing events; and
   detect the apnea events outside the excluded time periods, wherein the excluded time periods that the apnea events are impossible include:
   one or more time periods of the snoring events;

one or more time periods between two of the snoring events that are less than a pre-determined length of time;

one or more time periods between one of the conjunction spikes and one of the snoring events that are less than the pre-determined length of time;

one or more time periods between two of the conjunction spikes that are less than the pre-determined length of time; and one or more time periods of the breathing movement cessations that are less than the pre-determined length of time.

6. The system of claim 5, wherein the instructions when executed further cause the processor to:

count one apnea event outside the excluded time periods when one of the breathing movement cessations that is outside the excluded time periods lasts longer than the pre-determined length of time before one of the conjunction spikes that is outside the excluded time periods appears.

7. A system that expedites detecting apnea events of a user, comprising:

a sensing unit that captures one or more of a snoring sound of the user, a heart rate and a SPO2 value of the user, and a breathing movement of the user;

wherein a conjunction spike is a heart rate spike that occurs simultaneously with a SPO2 spike;

a data recorder that includes a clock and connects with the sensing unit, wherein the data recorder records measurements from the sensing unit and synchronizes the measurements in time by the clock; and a signal processing unit that extracts breathing events from the synchronized measurements, wherein the breathing events include snoring events, conjunction spikes, and breathing movement cessation, and that excludes time periods that an apnea event is impossible according to the breathing events so that detection of the apnea events is expedited, wherein the excluded time periods that the apnea events are impossible include:

a time period of each of the snoring events;

a time period between two of the snoring events that is less than a pre-determined length of time;

a time period between one of the conjunction spikes and one of the snoring events that is less than the pre-determined length of time;

a time period between two of the conjunction spikes that is less than the pre-determined length of time; and a time period of the breathing movement cessations that is less than the pre-determined length of time wherein the sensing unit further comprises:

an optic fiber;

an upper frame that is stiff; and a lower frame that is stiff and includes protrusions for holding the optic fiber therebetween, wherein the optic fiber is sandwiched between the upper frame and the lower frame, so that the optic fiber generates light loss corresponding to the breathing movements of the user when the user is lying on the upper frame.

8. The system of claim 7, wherein the signal processing unit counts one apnea event outside the excluded time periods when one of the breathing movement cessations outside the excluded time periods lasts longer than the pre-determined length of time before one of the conjunction spikes outside the excluded time periods appears.

9. A method executed by a computer for expediting detection of apnea events of a user, comprising:

receiving, by the computer, measurements captured from a plurality of sensors when the user is sleeping, wherein the measurements include snoring sounds, cardiovascular parameters and breathing movements of the user, and the measurements are synchronized by a clock;

using an optic fiber that is sandwiched between an upper frame and a lower frame so that the optic fiber generates light loss corresponding to the breathing movements of the user when the user is lying on the upper frame;

extracting, by the computer, a plurality of breathing events from the measurements, including snoring events, heart rate and SPO2 conjunction spikes, and breathing movement cessations;

wherein each heart rate and SPO2 conjunction spike is a heart rate peak that occurs simultaneously in time with a SPO2 peak;

excluding, by the computer, time periods that an apnea event is impossible according to a combination of the breathing events;

detecting, by the computer, the apnea events outside the excluded time periods that the apnea events are impossible, wherein the excluded time periods that the apnea events are impossible include:

a time period of each of the snoring events;

a time period between two of the snoring events that is less than a pre-determined length of time;

a time period between one of the heart rate and SPO2 conjunction spikes and one of the snoring events that is less than the pre-determined length of time;

a time period between two of the heart rate and SPO2 conjunction spikes that is less than the pre-determined length of time; and a time period of the breathing movement cessations that is less than the pre-determined length of time.

10. The method of claim 9, further comprising:

counting, by the computer, one apnea event outside the excluded time periods when one of the breathing movement cessations outside the excluded time periods lasts longer than the pre-determined length of time before one of the heart rate and SPO2 conjunction spikes outside the excluded time periods appears.

11. The method of claim 9, further comprising:

counting, by the computer, a number of the apnea events per hour.

* * * * *